United States Patent [19]

Bliss

[11] Patent Number: 4,576,163
[45] Date of Patent: Mar. 18, 1986

[54] SKIN MARKER FOR USE IN BIOPSY EXCISIONS

[76] Inventor: Robert J. Bliss, 925 W. H St., Jenks, Okla. 74037

[21] Appl. No.: 521,334

[22] Filed: Aug. 8, 1983

[51] Int. Cl.⁴ .............................................. A61F 17/32
[52] U.S. Cl. .................................................... 128/305
[58] Field of Search ..................... 128/316, 305, 305.5, 128/751

[56] References Cited

U.S. PATENT DOCUMENTS 2,932,296 4/1960 Sanders ................................ 128/305
4,192,312 3/1980 Wilson ................................. 128/305

Primary Examiner—Robert Peshock
Attorney, Agent, or Firm—Head, Johnson & Stevenson

[57] ABSTRACT

A surgical instrument for marking a pattern on the skin of a patient to first guide a surgeon in subsequently incising procedure to acquire an excision by a biopsy, or surgical debridement, with the use of a surgical cutting instrument, and secondly, provide guide indicia for accurately suturing or closing the excision defect to provide a straight hairline scar.

3 Claims, 5 Drawing Figures

U.S. Patent  Mar. 18, 1986  4,576,163
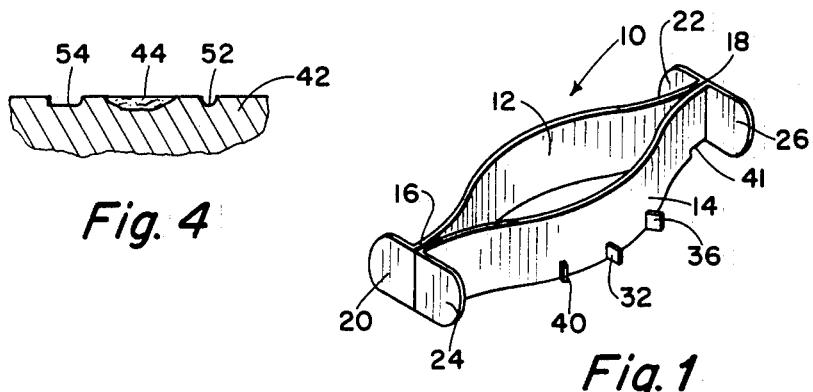
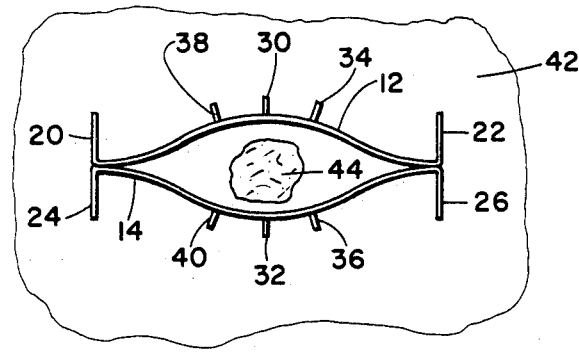
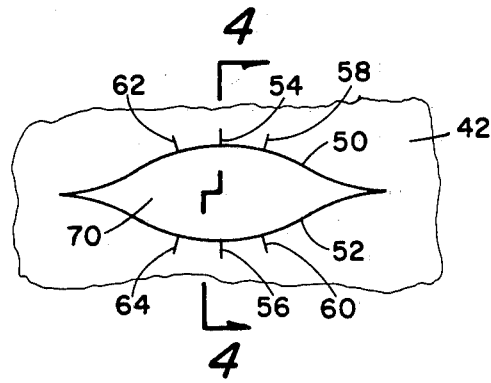
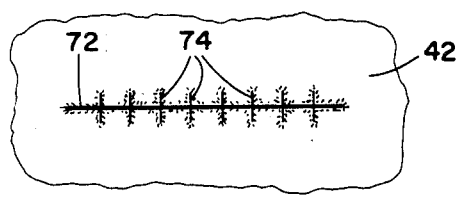

SKIN MARKER FOR USE IN BIOPSY EXCISIONS

BACKGROUND OF THE INVENTION

This invention is an improvement of prior U.S. Pat. No. 3,502,070 dated Mar. 24, 1970, in providing a surgeon guide indicia for accurately suturing an excision, the prior invention not having this feature. The result is accurate alignment of the side edges of the excised skin in the suturing process.

In connection with certain biopsies, especially in regard to a skin biopsy, it is desirable to excise a 'boat-shaped' or navicular section including both some healthy tissue as well as the lesion which is to be microscopically diagnosed. As used herein, the words 'boat-shaped' and 'navicular' have reference to a boat of the general character of a canoe or kayak in which the stern has the same shaping as the bow. An excision of this character leaves a remaining defect which may be accurately closed in a straight line and consequently a fine line straight scar results. Such a scar is preferable, as it can be made to fall in a natural skin line, such as a crease, wrinkle, and the like and thus be thereafter substantially unnoticeable. Further, straight scars spread less and are more apt to retain their hairline width than will curvate or puckered scars.

Difficulty has been experienced heretofore in making a biopsy excision, the result of which would be a straight hairline scar. Frequently the excision would not be of a proper boat shape, but, perhaps due to the elasticity of the skin, one side of the defect to be closed would be far more accurate than the other or one end of the defect would be far rounder than the other, so that repair of the defect would result in a scar curvature, puckered, or some other shape that would thereafter be noticeable.

SUMMARY OF THE INVENTION

With the foregoing in mind, it is an important object of this invention to provide a simple form of device which may be used on the skin of a patient to accurately define a proper boat-shaped area, thus indicating to the surgeon exactly where to incise in order to excise a properly boat-shaped section, leaving a defect that can be accurately closed to provide a straight hairline scar.

Also an object of this invention is the provision of a simple form of device which may easily be pressed against the skin of a patient and leave a slightly reddened and depressed line defining a properly boat-shaped area for an excision.

It is also a desideratum of this invention to provide a simple form of device by means of which a surgeon, in a single action, may mark upon the skin of a patient before incising an outline of an area where an excision is to be made.

A further significant object of this invention is to provide a device which accomplishes the above objects but also provides temporary marking or indicia on the skin of a patient along the side edges of the incising outline, which marks assist a surgeon in accurately suturing the incision side edges to close the defect caused by the excision.

BRIEF DESCRIPTION OF THE DRAWINGS

While some of the more salient features, characteristics and advantages of the instant invention have been above pointed out, others will become apparent from the following disclosures, taken in conjunction with the accompanying drawing in which:

FIG. 1 is an enlarged perspective view of a skin marker embodying principles of this invention.

FIG. 2 is a fragmentary plan view illustrating the use of the invention in marking the skin around a lesion;

FIG. 3 is a fragmentary plan view of the defect remaining after the excising of a section for biopsy;

FIG. 4 is a fragmentary vertical section view taken substantially as indicated by the line 4—4 of FIG. 3, looking in the direction of the arrows;

FIG. 5 is a fragmentary plan view of the repaired defect indicating the scar to result.

DETAILED DESCRIPTION OF THE PREFERRED EMBODIMENT

Before explaining the present invention in detail, it is to be understood that the invention is not limited in its application to the details of construction and arrangement of parts illustrated in the accompanying drawings, since the invention is capable of other embodiments and of being practiced or carried out in various ways commensorate with the claims herein. Also it is to be understood that the phraseology or terminology employed herein is for the purpose of description and not of limitation.

The illustrated embodiment of the instant invention may be made of sheet metal such as stainless steel, or a fairly rigid sheet plastic material, or any other suitable material. The completed skin marker, generally indicated by numeral 10 and seen in FIG. 1 may be formed from a pair of like blanks 12 and 14 which join at the ends 16 and 18 to form the 'boat-shaped' device as shown. Each blank includes respective end tabs 20 and 22 for blank 12 and tabs 24 and 26 for blank 14. The tabs provide a surface to hold and use between a thumb and finger of a surgeon's hand. Extending outwardly of each blank at the bottom thereof are one or more suture guide markers identified as center markers 30 and 32 and side markers 34, 36, 38 and 40. The joined ends include a recess 41, raising the tab ends above the bottom of the marker surfaces.

In assembling the blanks, the central portions of the blanks are bowed outwardly in opposite directions and the end edges of the blanks are brought into confronting relationship and secured together maintaining the boat shape of the marker. If the blanks are made of metal, silver solder may be used to join the blanks at the ends thereof and the tabs to the margins, while if the blanks are made of thermoplastic material, the parts may be joined together in those locations by fusing. If other materials are used, they may be joined in the manner common with such materials.

The invention may be made in various sizes so that the surgeon may have available a plurality of markers graduating in size. In use, it is a simple expedient for the surgeon to select the proper size marker for the particular lesion to be excised, and press it upon the skin 42 of a patient around a lesion 44, as shown in FIG. 2. It will be noted that when the mark is evenly disposed around the lesion, the situs of the lesion is perfectly visible to the surface through the central portion of the marker, so accurate placing of the marker is a simple expedient. Then a gentle but firm pressure of the marker against the skin leaves slightly reddened or discolored and depressed lines 50 and 52, formed in the skin after removal by blanks 12 and 14, and marks 54, 56, 58, 60, 62 and 64, formed in the skin by respective suture markers 30, 32, 34, 36, 38, and 40. The lines 50 and 52 thus defining the area of the proposed excision. It will also be noted that the line indicates plainly to the surgeon just where to make his initial incision or incisions and such marking can readily be followed by the surgeon regardless of the elasticity of the skin.

After the excision has been accomplished in a known manner, a defect 70 as seen in FIG. 3 will remain. It will be noted that the defect is of the proper boat shape with the side walls thereof of the same general contour with only negligible, if any, relative variation. This defect 70 can therefore be repaired by bringing the side edges thereof together to form a fine straight line 72 as shown in FIG. 5, which defines an ultimate scar of hairline width and which is practically unnoticeable thereafter. In order to accurately suture the side edges, a surgeon need only align marks 54 to 56, 58 to 60, 62 to 64, etc. The sides of the defect may be sutured together in any desired manner, such as by an over-and-over suture not being critical, but shown by way of example.

The skin marker is durable, and may be repeatedly used throughout a long life, accurately retaining its shape. The marker is economical to manufacture, the illustrated embodiment including only identical stampings, and may be economically utilized because of its long life. It will also be noted that, if deemed necessary, the cutter may be effectively sterilized between uses.

While the instant invention has been hereinabove disclosed and described in connection with a skin biopsy, it will be apparent to those skilled in the art that the marker may be utilized for other purposes, such as a surgical debridement in some cases, as will be apparent to one skilled in the art. It should also be noted that by varying the contour of the marker locations for various types of incisions may be marked upon the body of a patient.

What is claimed is:

1. A skin marker for surgical purposes, comprising a hollow member of material sufficiently rigid to leave a marking on the skin of a patient after being pressed edgewise thereagainst, said members being formed of a pair of initially flat blanks disposed on edge with their ends secured tightly together and each blank being outwardly bowed centrally thereof to define a bottom edge having an excision pattern converging to a point at each end from a widened central area to leave a defect after incision that may be closed to provide a fine line straight scar, each blank of said pair being a mirror image of each other with each blank having at least one suture guide marker extending outwardly of each blank, the bottom edge of said marker being in the same plane as said bottom edge of said blank.

2. The skin marker of claim 1 wherein each of said blanks have three spaced suture markers.

3. The skin marker of claim 1 wherein each of said ends of said blanks include an outwardly extending tab, the bottom of said tabs recessed above said bottom edge.

* * * * *